United States Patent
Ciota et al.

(10) Patent No.: US 6,214,627 B1
(45) Date of Patent: Apr. 10, 2001

(54) RAPID COLORIMETRIC METHOD FOR MEASURING POLYMERS IN AQUEOUS SYSTEMS

(75) Inventors: Steven R. Ciota, Downers Grove; John E. Hoots, St. Charles, both of IL (US)

(73) Assignee: Nalco Chemical Company, Naperville, IL (US)

( * ) Notice: Subject to any disclaimer, the term of this patent is extended or adjusted under 35 U.S.C. 154(b) by 0 days.

(21) Appl. No.: 09/277,275

(22) Filed: Mar. 26, 1999

(51) Int. Cl.[7] .................................................... G01N 21/78
(52) U.S. Cl. ........................... 436/166; 436/85; 436/128; 436/164; 436/175; 436/177; 436/808; 422/61
(58) Field of Search ................................. 436/6, 56, 85, 436/104, 119, 120, 128, 129, 171, 172, 808, 166; 422/61

(56) References Cited

U.S. PATENT DOCUMENTS

| | | |
|---|---|---|
| 4,894,346 | 1/1990 | Myers et al. . |
| 5,342,787 * | 8/1994 | Bardsley et al. ..................... 436/179 |
| 5,389,548 | 2/1995 | Hoots et al. . |

OTHER PUBLICATIONS

"Turbidity Science", Technical Information Series, Booklet No. 11, Michael J. Sadler, HACH Technical Center for Applied Analytical Chemistry, ©1982, 1984, 1985, 1989, 1996, 1998.

TRANSPORT–PLUS® DR/2000 Procedure, Nalco Chemical Company, ©1995.

"Polyacrylic Acid Absorption–Colorimetric Method", from the HACH Water Analysis Handbook, ©1997.

Calgon Patent (#0144130) Test Procedure, In use Effective Apr. 13, 1989.

* cited by examiner

*Primary Examiner*—Lyle A. Alexander
(74) *Attorney, Agent, or Firm*—Margaret M. Brumm; Thomas M. Breininger (57) ABSTRACT

A method for measuring the concentration of an anionically charged polymer in an aqueous solution is described and claimed. The method requires a reagent solution that is also described and claimed. The reagent solution comprises water, Nile Blue Dye and chelant, with the chelant being selected from the group consisting of the alkali metal or ammonium salts of phosphonobutane tricarboxylic acid. The method involves using absorbance measurements to determine the amount of anionically charged polymer present in an aqueous sample. The method is very rapid and thus is very useful under field conditions.

20 Claims, 7 Drawing Sheets

the level of TRANSPORT-PLUS® polymer.

RAPID COLORIMETRIC METHOD FOR MEASURING POLYMERS IN AQUEOUS SYSTEMS

FIELD OF THE INVENTION

The present invention relates generally to the detection of water-soluble polymers in industrial water systems such as cooling water systems and boiler water systems. More specifically, the present invention relates to a method of determining the concentration or availability of anionic water-soluble polymers in industrial water systems wherein said polymers are employed to prevent the formation of scales and/or deposits.

BACKGROUND OF THE INVENTION

Water is used as a coolant in a number of industrial processes as well as in the generation of steam. However, undistilled or untreated water contains a number of impurities which can affect heat transfer, fluid flow or cause corrosion of process equipment. Accordingly, when municipal or untreated water is utilized for cooling or steam formation, the water must be treated with appropriate chemicals in order to inhibit scale formation on industrial equipment.

Typically, the problematic impurities in water are metal cations, such as calcium, barium, magnesium and sodium as well as some anions, such as bicarbonate, carbonate, sulfate, phosphate, silicate and fluoride. When the water contains an excess of these anions and cations precipitates are known to form on equipment surfaces in the form of scales or deposits.

The presence of the scales or deposits adversely affects the rate of heat transfer and therefore the efficiency of the system. Further, the cleaning or removal of such scales or deposits is expensive because it typically requires a shutdown of the system.

A number of chemicals have been provided to reduce or inhibit scale and deposit formation in industrial water systems. More specifically, water-soluble polymers that are anionically charged have proven useful. One particularly useful water-soluble polymer is polyacrylic acid and modified polyacrylic acid; although other water-soluble polymers that are at least partially anionically charged are in use as well.

However, the employment of water-soluble polymers in industrial water systems presents its own set of problems, because the concentration of the polymers in the water must be carefully monitored. For example if too high a concentration of the polymer is employed, then the cost/performance efficiency of the system is adversely affected. In contrast, if too little of the polymer is employed, scaling and/or deposition and/or corrosion will occur. As with other chemical treatment of aqueous systems, there is an optimal concentration that should be maintained.

Methods for determining the concentration of water-soluble polymers in aqueous systems are available. For example, there is a patented fluorometric method for determination of polyelectrolytes using fluorochromatic dyes, see U.S. Pat. No. 5,389,548, which is incorporated by reference. Other current methods for determining the concentration of water-soluble polymers in aqueous systems rely, in part, upon the formation of turbidity, with such principles of such processes described in the reference, "Turbidity Science", by Michael J. Sader, Technical Information Series—Booklet No. 11, from the HACH Technical Center for Applied Analytical Chemistry. One such method is the TRANSPORT-PLUS® DR/2000 Procedure from Nalco Chemical Company. The TRANSPORT-PLUS® DR/2000 Procedure is a multi-step absorbance based turbidimetric method that takes approximately 20 minutes to determine the level of TRANSPORT-PLUS® polymer.

A colorimetric method is the Hach polyacrylic acid method (Method 8107 from Hach, telephone number (800) 227-4224). The Hach polyacrylic method uses iron thiocyanate chelation to detect polymers with calibrations based on polyacrylic acid products. The known turbidimetric methods and the Hach method suffer from extensive absorption/desorption/washing processing steps with multiple reagents and long reaction times.

There is another colorimetric analytical method recited in U.S. Pat. No. 4,894,346, (hereinafter the '346 patent). The method described in the '346 patent is relatively complicated and difficult to carry out in the field. When conducting the method described in the '346 patent, the pH of the water sample must be adjusted, at the outset, prior to the combination of the sample with the reagent which contains the dye.

A data sheet describing this colorimetric method (based on the European patent application corresponding to the '346 patent) includes in the procedure a waiting period of 30 minutes for completion of the reaction necessary to finish the analysis. Under field conditions thirty minutes is too long a time to wait for the method to be practical. Accordingly, there is a need for an improved colorimetric method for measuring the concentration of water-soluble polymers in aqueous systems that is easier, more accurate, more selective and faster to conduct than the currently available methods.

Yet another disadvantage associated with currently available colorimetric and turbidimetric measuring methods is their intolerance to ions and other contaminants commonly present in municipal and industrial water systems. For example, currently available colorimetric methods such as those described in the '346 patent are susceptible to inaccuracy in highly alkaline systems, highly acidic systems or where the presence of ions or other impurities exceeds certain concentrations. Turbidimetric methods are even more susceptible to inaccuracies caused by the presence of ions and other contaminants then are colorimetric methods. Accordingly, there is a need for an improved method for measuring the concentration of polymers in aqueous systems that is more tolerant of common contaminants and other common properties of municipal and industrial waters.

SUMMARY OF THE INVENTION

The first aspect of the present invention is a method for measuring the concentration of an anionically charged polymer in an aqueous solution that comprises the steps of:
(a) providing a reagent solution comprising
  i) water,
  ii) Nile Blue Dye; and
  iii) chelant, with said chelant being selected from the group consisting of the alkali metal or ammonium salts of phosphonobutane tricarboxylic acid;
(b) using a suitable device to measure the absorbance of said reagent solution by itself and using this absorbance measurement to zero said suitable device at the level of 0 ppm polymer concentration;
(c) providing a sample of an aqueous solution containing at least one anionically charged polymer to be tested,
(d) combining said reagent solution and said sample to create a mixture, (e) measuring the absorbance of the mixture using the same suitable device used in step (b); and (f) comparing the absorbance of the mixture with the absorbance of samples containing known concentrations of the anionically charged polymers and determining the concentration of anionically charged polymer in the sample therefrom;

wherein the method is conducted without adjusting the pH of said sample and wherein the method further comprises the step of waiting a time period of less than about 7 minutes for said reagent solution and said anionically charged polymer to react between the (d) combining step and the (e) measuring step.

The second aspect of the present invention is a method for measuring the concentration of an anionically charged polymer in an aqueous solution that comprises the steps of:

(a) providing a reagent solution comprising
  i) water,
  ii) Nile Blue Dye; and
  iii) chelant, which is phosphonobutane tricarboxylic acid;

(b) using a suitable device to measure the absorbance of said reagent solution by itself and using this absorbance measurement to zero said suitable device at the level of 0 ppm polymer concentration;

(c) providing a sample of an aqueous solution containing at least one anionically charged polymer to be tested, (d) combining said reagent solution and said sample to create a mixture, (e) measuring the absorbance of the mixture using the same suitable device used in step (b); and (f) determining the concentration of anionically charged polymer containing a measurable amount of at least one strongly acidic moiety; wherein the method is conducted without adjusting the pH of said sample and wherein the method further comprises the step of waiting a time period of less than about 7 minutes for said reagent solution and said anionically charged polymer to react between the combining step and the measuring step.

The third aspect of the present invention is a reagent solution comprising:

(i) water,
(ii) Nile Blue Dye; and
(iii) chelant, with said chelant being selected from the group consisting of the alkali metal or ammonium salts of phosphonobutane tricarboxylic acid.

The fourth aspect of the present invention is a reagent solution comprising:

(i) water,
(ii) Nile Blue Dye; and
(iii) chelant, which is phosphonobutane tricarboxylic acid.

DETAILED DESCRIPTION OF THE PREFERRED EMBODIMENTS

The present invention provides an improvement to prior art methods in that the method is carried out in essentially three simple steps: the absorbance of the reagent solution is measured, a specified amount of the water sample is added to the dye solution, and the absorbance of the reagent/polymer solution mixture is then measured.

In creating the reagent solution needed to conduct this analysis, either Nile Blue A (Chemical Abstracts Service Reg. No. 3625-57-8) or Nile Blue chloride (CAS Reg. No. 2381-85-3) can be utilized as the reagent dye. Both Nile Blue A and Nile Blue chloride are available from Aldrich Chemical Company, P.O. Box 2060, Milwaukee, Wis.

53201, telephone numbers 414-273-4979 or 1-800-558-9160. Hereinafter, the phrase "Nile Blue Dye" will be used to mean either Nile Blue A or Nile Blue chloride or a mixture of Nile Blue A and Nile Blue chloride. Even though it is possible to use Nile Blue chloride by itself or in combination with Nile Blue A, the preferred reagent dye is Nile Blue A by itself.

The appropriate amount of Nile Blue Dye, present in the reagent solution is from about 4.7 ppm to about 9.0 ppm, preferably from about 5.3 ppm to about 8.5 ppm and most preferably about 6.9 ppm.

The chelant used in the reagent solution is an alkali metal or ammonium salt of phosphonobutane tricarboxylic acid. The preferred phosphonobutane tricarboxylic acid is 2-phosphonobutane-1,2,4-tricarboxylic acid. The alkali metal salts include, but are not limited to, the sodium salt, the potassium salt and the lithium salt. The preferred chelant is 2-phosphonobutane-1,2,4-tricarboxylic acid, sodium salt.

2-Phosphonobutane-1,2,4-tricarboxylic acid is available from Bayer, 100 Bayer Road, Pittsburgh, Pa. 15205-9741, telephone number: (800) 662-2927. One way to create the sodium salt of phosphonobutane tricarboxylic acid is to contact the phosphonobutane tricarboxylic acid with a suitable reagent, such as sodium hydroxide.

The concentration of chelant in the reagent solution, is from about 55 ppm to about 1100 ppm, preferably from about 500 ppm to about 600 ppm and most preferably about 550 ppm. Reagent solution with about 550 ppm of chelant is hereinafter referred to as "JARGON". Reagent solution with more than about 550 ppm of chelant, is hereinafter referred to as "super-JARGON". Reagent solution with less than about 550 ppm of chelant is hereinafter referred to as "lite-JARGON".

It is also possible to create a reagent solution using chelant which is phosphonobutane tricarboxylic acid. A reagent solution using chelant that is phosphonobutane tricarboxylic acid will hereinafter be referred to as A-JARGON. The amount of phosphonobutane tricarboxylic acid present in A-JARGON is preferably from about 300 ppm to about 2200 ppm, more preferably from about 500 ppm to about 600 ppm and most preferably about 550 ppm. It is possible to create A-JARGON that contains as little as 55 ppm phosphonobutane tricarboxylic acid, however, in order to use any A-JARGON containing less than about 300 ppm phosphonobutane tricarboxylic acid, the pH of the A-JARGON must be adjusted to less than about 3 using a suitable reagent. Suitable reagents for this purpose, include, but are not limited to, hydrochloric acid, sulfuric acid or nitric acid.

Reagent solution with about 550 ppm of phosphonobutane tricarboxylic acid is hereinafter referred to as "normal A-JARGON". Reagent solution with more than about 550 ppm of phosphonobutane tricarboxylic acid, is hereinafter referred to as "super A-JARGON". Reagent solution with less than about 550 ppm of phosphonobutane tricarboxylic acid is hereinafter referred to as "lite A-JARGON".

A-JARGON is useful only for detecting polymers containing strongly acidic moieties. These strongly acidic moieties include, but are not limited to, sulfonate, sulfate, phosphonate and phosphate moieties.

The remainder of the reagent solution is water that has either been distilled or deionized or otherwise treated to remove possible contaminants.

In order to make reagent solution, it has been found preferable to first make an aqueous "stock" solution of Nile Blue Dye and a separate aqueous "stock" solution of chelant. Hereinafter the aqueous "stock" solution of chelant will be referred to as "Chelant" stock solution if the chelant is an alkali metal or ammonium salt of phosphonobutane tricarboxylic acid. If the chelant is phosphonobutane tricarboxylic acid, then the stock solution of chelant is referred to as "A-Chelant" stock solution.

The concentration of Nile Blue Dye in the stock solution is from about 43 ppm to about 81 ppm, preferably from about 48 ppm to about 76 ppm and most preferably about 62 ppm. The concentration of chelant in the Chelant stock solution is from about 500 ppm to about 10,000 ppm, preferably from about 4500 ppm to about 5000 ppm and most preferably about 5000 ppm. The concentration of phosphonobutane tricarboxylic acid in the stock solution of A-Chelant is from about 500 ppm to about 10,000 ppm, preferably from about 4500 ppm to about 5000 ppm and most preferably about 5000 ppm.

In practice it has been found that the stock solution of Nile Blue Dye, the stock solution of Chelant and the stock solution of A-chelant are all stable for many months, thus ensuring that they can be made in advance and used as necessary.

Once the appropriate amounts of stock solution of Nile Blue Dye and Chelant or A-Chelant stock solution are added to the appropriate amount of water to make JARGON or super-JARGON or lite-JARGON or A-JARGON or super A-JARGON or lite A-JARGON, the absorbance of the reagent solution, by itself, is measured in order to zero the instrument used. The absorbencies may be measured using any suitable device known in the art to measure absorbance. Such suitable devices, include, but are not limited to colorimeters, spectrophotometers, color-wheels and other types of known color-comparitor measuring tools. The preferred suitable devices are spectrophotometers and colorimeters. Preferred spectrophotometers include the currently available DR/2010 spectrophotometer, which is available from Hach Company, 5600 Lindbergh Drive, P.O. Box 389, Loveland, Colo. 80539-0389; telephone numbers: (800) 227-4224 or (970) 669-3050. To use the DR/2100 spectrophotometer for this work, it is set at a wavelength of 635 nm, with a cell path length of 1 inch. Preferred colorimeters include the currently available DR/890 Colorimeter, which is also available from Hach Company. To use the DR/890 Colorimeter for this work, it is set at a wavelength of 610 nm, with a round cell path length of 2.5 centimeters.

In order to determine the concentration or amount of available anionic polymer in an industrial water system it is first necessary to generate "calibration curves" for each polymer of interest. Calibration curves are generated by preparing samples of water containing known amounts of polymer, making an appropriate reagent solution and measuring the absorbance of the sample using the reagent solution. For purposes of this work absorbance is being reported as absorbance difference. Absorbance difference is the difference between the absorbance of the reagent solution by itself and the absorbance of the mixture of reagent solution and the sample of water being tested. The calibration curve is then a plot of this absorbance difference vs. the known concentration of polymer in the sample. Once created the calibration curve can be used to tell how much polymer is present in a sample by comparing the measured absorbance difference of the sample with the curve and reading the amount of polymer present off of the curve. In order to use a calibration curve, the reagent solution used to test the sample must have the same type and concentration of chelant as was present in the reagent solution that was used to create the curve. Furthermore, in order to use a calibration curve, the suitable device to measure absorbance must also be the same as the suitable device that was used to create the calibration curve.

FIG 1 and FIG. 2 and FIG. 3 and FIG. 4 and FIG. 5 and FIG. 6 and FIG. 7 all illustrate calibration curves for certain anionic polymers. All of these calibration curves were generated using JARGON reagent solution. Once created, calibration curves can be repetitively used for determining the concentration of the desired anionic polymer in the sample of water being tested.

In order to determine the concentration of anionic polymer in a sample of water using this method, 1 ml of the water sample is combined with 25 ml of the reagent solution. Before the water sample is combined with the reagent solution it is preferred that the water sample be filtered. The preferred filter is a 0.45-micron filter. The 1 ml of water sample and 25 ml of reagent solution may be measured out using conventional pipettes. It is possible to conduct the instant claimed method by adding the 25 ml of the reagent solution to the 1 ml of filtered water sample, however it is preferred that the 1 ml of filtered water sample be added to 25 ml of the reagent solution because this facilitates measuring.

The anionic polymer in the sample is then allowed to react with the reagent solution for no more than about 7 minutes, preferably less than about 2 minutes, more preferably less than about 1 minute and most preferably for about 30 seconds. It has been found that the reaction is usually complete in about 30 seconds, making any absorbance measurement taken at about 30 seconds and thereafter accurate. It has been found that this accurate absorbance measurement remains essentially stable for the first seven minutes of time, with minor fluctuations occurring after the first seven minutes. Once the absorbance of the sample and reagent solution is measured (usually as the absorbance difference described above), it is compared with calibration curves that show the standard absorbance of solutions containing known amounts of the specific anionic polymer. In this way, the amount of anionic polymer present in the sample can be determined.

FIG. 1 and FIG. 2 and FIG. 3 and FIG. 4 and FIG. 5 and FIG. 6 and FIG. 7 all illustrate calibration curves for certain anionic polymers using either a spectrophotometer or a calorimeter. Calibration curves are easily generated, as described previously, and can be posted on site or stored electronically for determining the concentration of the desired anionic polymer in the sample of water being tested.

Polymers capable of being detected by the method of the instant claimed invention include, but are not limited to, polyacrylic acid moiety polymers with functional groups resulting in at least a partial anionic charge for the polymer, and polysufonated polymers and maleic anhydride polymers.

Polyacrylic acid moiety polymers include homopolymers, copolymers, terpolymers and tetrapolymers. Functional groups resulting in at least a partial anionic charge, include carboxylate, sulfonates, organic sulfonate, phenolic, phosphonate, organic phosphate and mixtures thereof. The polymer may also be amphoteric, or a mixture of anionic and cationic charged, as long as a sufficient pre-dominance of anionic charge exists on the polymer.

Polysufonated polymers include, but are not limited to, polystyrene sulfonic acid polymers and polyvinyl sulfonic acid polymers.

Examples of polymers that can be detected using the method of the instant claimed invention can be found in U.S. Pat. Nos. 4,752,443; 4,756,881; 4,801,388; 4,869,828; 4,898,686; 4,929,425; 4,963,267; 4,973,428; and 5,128,419.

Preferred polymers in cooling water treatment, include, but are not limited to, polyacrylic acid homopolymer, copolymers of acrylic acid and acrylamide and post-polymerization derivatized terpolymers of acrylamide/acrylic acid and either acrylamido ethane sulfonic acid or acrylamido methane sulfonic acid. These preferred polymers include, but are not limited to, a terpolymer of acrylic acid (about 60 to 70 mole %), acrylamide (about 9 to 27 mole %) and acrylamidomethanesulfonic acid, sodium salt (about 13 to 21 mole %) with a weight average molecular weight of between about 14,000 and about 25,000 Daltons; a terpolymer of acrylic acid (about 40 to 50 mole %), acrylamide (about 15 to 35 mole %) and acrylamidomethanesulfonic acid, sodium salt (about 25 to 35 mole %), said terpolymer having a weight average molecular weight of between about 20,000 and 35,000 Daltons; a polyacrylic acid, sodium salt homopolymer, with a weight average molecular weight of between about 2500 and about 4000 Daltons; a copolymer of acrylic acid (about 90 mole %) and styrenesulfonic acid, sodium salt (about 10 mole %) with a weight average molecular weight of between about 25,000 and about 50,000 Daltons; and a copolymer of acrylic acid (about 99 mole %) and styrenesulfonic acid, sodium salt (about 1 mole %) with a weight average molecular weight of between about 7000 and about 10,000 Daltons.

Copolymers of acrylic acid and acrylamide are available from Nalco Chemical Company under the Transport Plus® trademark. Terpolymers of acrylamide/acrylic acid and acrylamido methane sulfonic acid are available from Nalco Chemical company under the PRISM® trademark. The remainder of these polymers are known to persons of ordinary skill in the art.

The instant claimed method is capable of detecting polymers at a level of about 0.6 ppm to about 20 ppm. It is possible to extend this range by modifying the sample and reagent solution size. These modifications would be within the scope of a person of ordinary skill in the art. It is to be understood that if either the size of the sample or the size of the reagent solution is modified then calibration curves will have to be generated for the new sample sizes. For example, all of the calibration curves included in this patent application were generated using a water sample size of 1 ml and a reagent solution size of 25 ml.

When conducting the method of the instant claimed invention, it has been found that when using JARGON the method is still viable (viability defined as measured values obtained within ±10% of actual polymer concentrations) even when the species listed in Table 1 are present in the sample at or below the indicated concentrations. The method is still viable when the sample has a pH in the indicated pH range. It is also to be understood that these operating ranges can be adjusted by changing the ratio of reagent solution to water sample or adjusting the chelant level in the reagent solution. This tolerance of contaminants is a huge advantage over the known turbidimetric and colorimetric methods of analysis, which cannot tolerate such levels of contaminants.

TABLE 1

| | | | |
|---|---|---|---|
| Alkalinity ($HCO_3$ as $CaCO_3$) | 1800 ppm | Manganese (as $Mn^{+2}$) | 860 ppm |
| | | Molybdate (as $MoO_4^{2-}$) | 870 ppm |
| Alkalinity ($CO_3^{-2}$ as $CaCO_3$) | 600 ppm | pH | 4.5–11.0 |
| Aluminum (as $Al^{+3}$) | 120 ppm | Hexamethaphosphate (as $PO_4$) | 4 ppm |
| Barium (as $Ba^{2+}$) | 770 ppm | | |
| Benzotriazole (as BZT) | 1500 ppm | Tripolyphosphate (as $PO_4$) | 300 ppm |
| Bisulfate (as $HSO_4^-$) | 1800 ppm | Nickel (as $Ni^{2+}$) | 200 ppm |
| Boron (as B) | 280 ppm | Nitrate (as $NO_3^-$) | 1600 ppm |
| Bromide (as $Br^-$) | 3300 ppm | Nitrite (as $NO_2^-$) | 2300 ppm |
| Calcium (as $CaCO_3$) | 1700 ppm | Orthophosphate (as $PO_4$) | 2100 ppm |
| Chloride (as $Cl^-$) | 3000 ppm | Pyrophosphate (as $PO_4$) | 370 ppm |
| Chromate (as $CrO_4$) | 600 ppm | Silicate (as $SiO_2$) | 530 ppm |
| Chromium (as $Cr^{6+}$) | 270 ppm | Sodium (as $Na^+$) | 2000 ppm |
| Conductivity | 6000 μS/cm | Strontium (as $Sr^{2+}$) | 80 ppm |
| Copper (as $Cu^{2+}$) | 660 ppm | Sulfate (as $SO_4^{-2}$) | 1700 ppm |
| Chlorine (free as $Cl_2$) | 10 ppm | Sulfite (as $SO_3$–2) | 1300 ppm |
| Glass H (as $PO_4$) | 4 ppm | Tolyltriazole (as TT) | 1100 ppm |
| HEDP (as $PO_4$) | 1400 ppm | Turbidity (after filtration) | 120 ppm |
| Iron (as $Fe^{3+}$) | 4 ppm | Zinc (as $Zn^{+2}$) | 400 ppm |
| Iron (as $Fe^{2+}$) | 90 ppm | | |
| Magnesium (as $CaCO_3$) | 1700 ppm | | |

The following examples are intended to be illustrative of the present invention and to teach one of ordinary skill how to make and use the invention. These Examples are not intended to limit the invention or its protection in any way.

EXAMPLES

Example 1

Making and Testing of JARGON

The Nile Blue A Stock solution is made by adding 0.0619 grams of 82% Nile Blue A dye to 1 liter of distilled water.

Chelant solution is made by diluting to 1 liter, 10 grams of a 50% aqueous solution of 2-phosphonobutane-1,2,4-tricarboxylic acid. Sufficient sodium hydroxide is then added to create the sodium salt of phosphonobutane tricarboxylic acid. The pH of the Chelant solution ranges from about 7 to about 9 and preferably from about 7.5 to about 8.5. The Chelant solution is then brought to the desired volume of 1 Liter by adding sufficient distilled water. The resulting Chelant solution contains 5000 ppm of phosphonobutane tricarboxylic acid, sodium salt.

The next step is to take 111 ml of the Chelant solution and combine it with 111 ml of the Nile Blue A stock solution and about 300 ml of distilled water. This combined solution is then made-up to 1 liter using distilled water and mixed thoroughly to provide a reagent solution with a level of phosphonobutane tricarboxylic acid, sodium salt, of about 550 ppm, namely JARGON.

The absorbance of the JARGON is then measured using a DR 2010 Spectrophotometer, set at 635 nm with a cell path length of 1 inch and this absorbance value is then used to "zero" the instrument.

The next step is to add 1 ml of filtered water sample to 25 ml of JARGON. After waiting 30 seconds the absorbance is measured. The measured absorbance value is compared with calibration curves showing the absorbance of samples containing known amounts of polymer.

Figure 1:
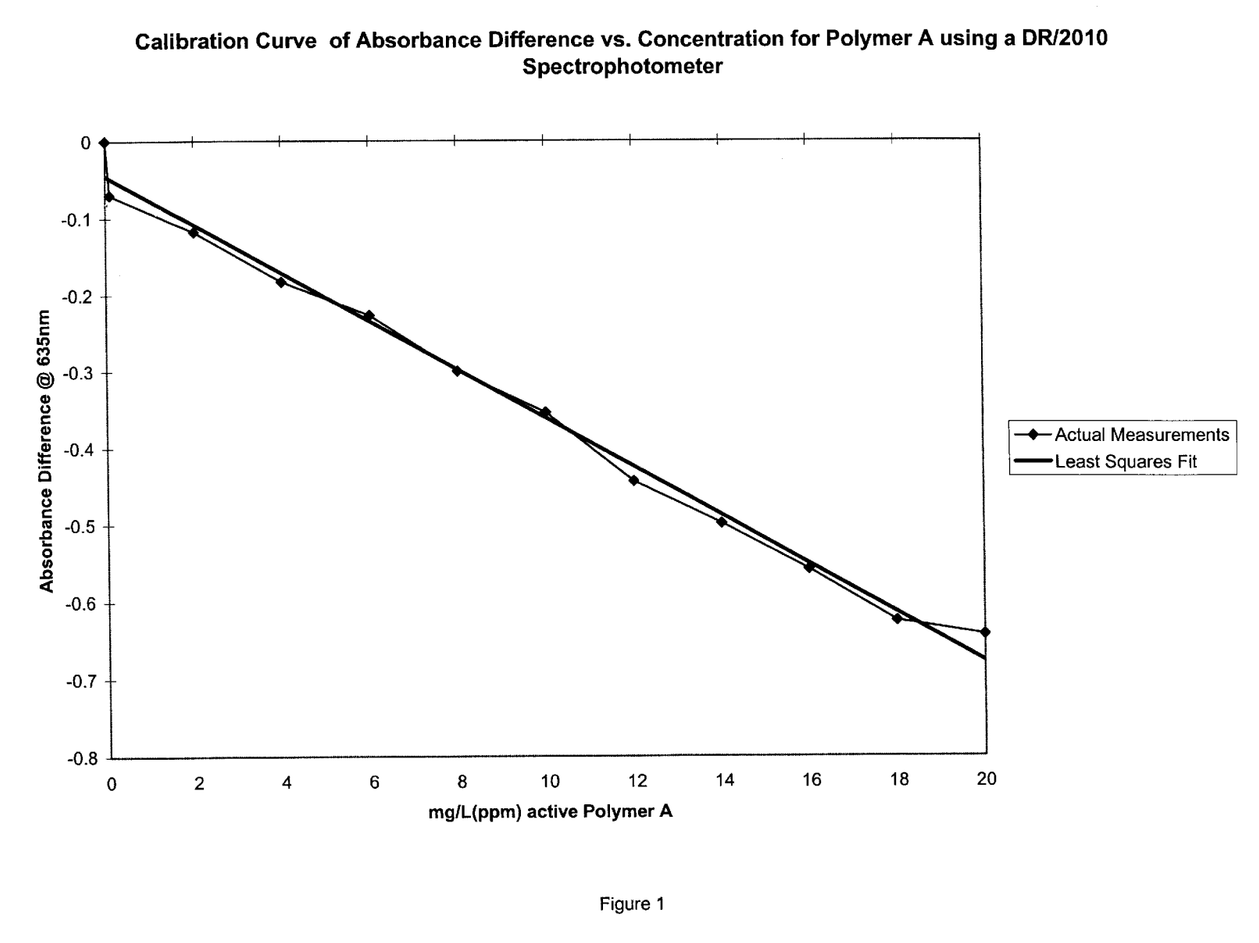
FIG. 1 illustrates, graphically, a calibration curve of absorbance difference versus polymer concentration (in mg/Liter) at 635 nanometers (hereinafter "nm") for Polymer A using a DR 2010 Spectrophotometer. Polymer A is a terpolymer of acrylic acid (about 60 to 70 mole %), acrylamide (about 9 to 27 mole %) and acrylamidomethanesulfonic acid, sodium salt (about 13 to 21 mole %) with a weight average molecular weight of between about 14,000 and about 25,000 Daltons. One of the lines is a plot of the actual measurements taken, the other line was drawn using a least squares fit to the data.
Figure 2:
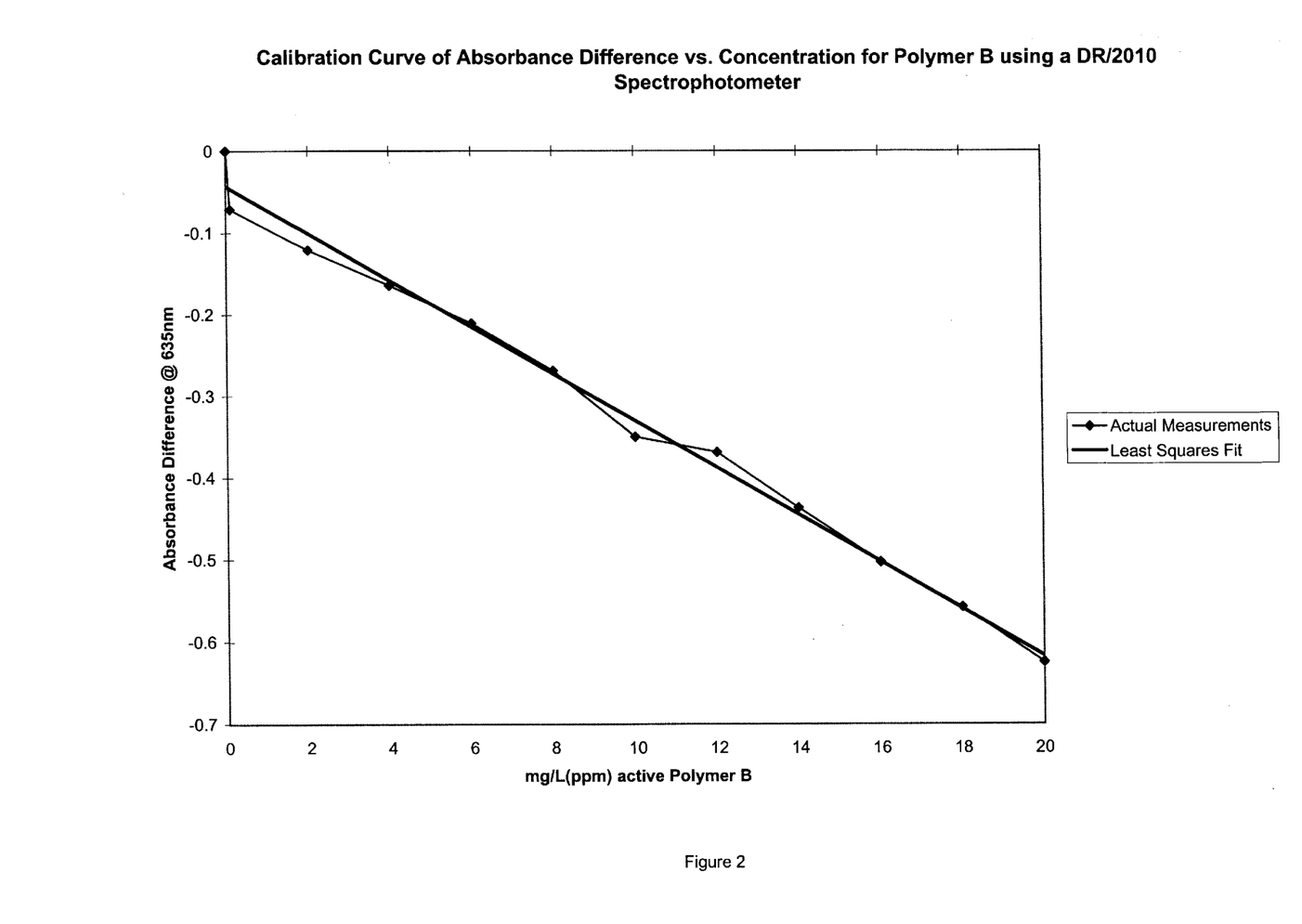
FIG. 2 illustrates, graphically, a calibration curve of absorbance difference versus polymer concentration (in mg/Liter) at 635 nm for Polymer B using a DR 2010 Spectrophotometer. Polymer B is a terpolymer of acrylic acid (about 40 to 50 mole %), acrylamide (about 15 to 35 mole %) and acrylamidomethanesulfonic acid, sodium salt (about 25 to 35 mole %), said terpolymer having a weight average molecular weight of between about 20,000 and 35,000 Daltons. One of the lines is a plot of the actual measurements taken, the other line was drawn using a least squares fit to the data.
Figure 3:
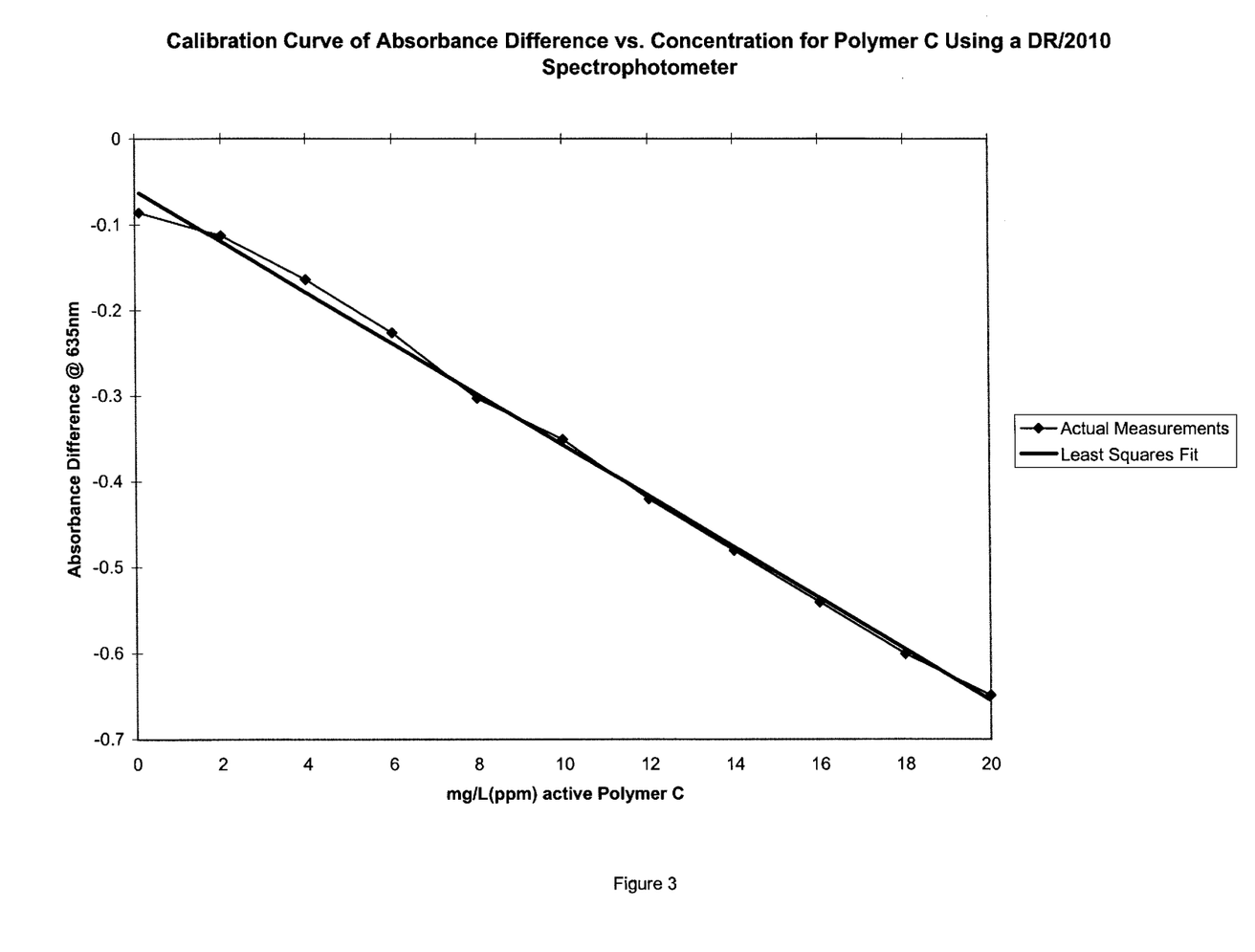
FIG. 3 illustrates, graphically, a calibration curve of absorbance difference versus polymer concentration (in mg/Liter) at 635 nm for Polymer C using a DR 2010 Spectrophotometer. Polymer C is a polyacrylic acid, sodium salt homopolymer, with a weight average molecular weight of between about 2500 and about 4000 Daltons. One of the lines is a plot of the actual measurements taken, the other line was drawn using a least squares fit to the data.
Figure 4:
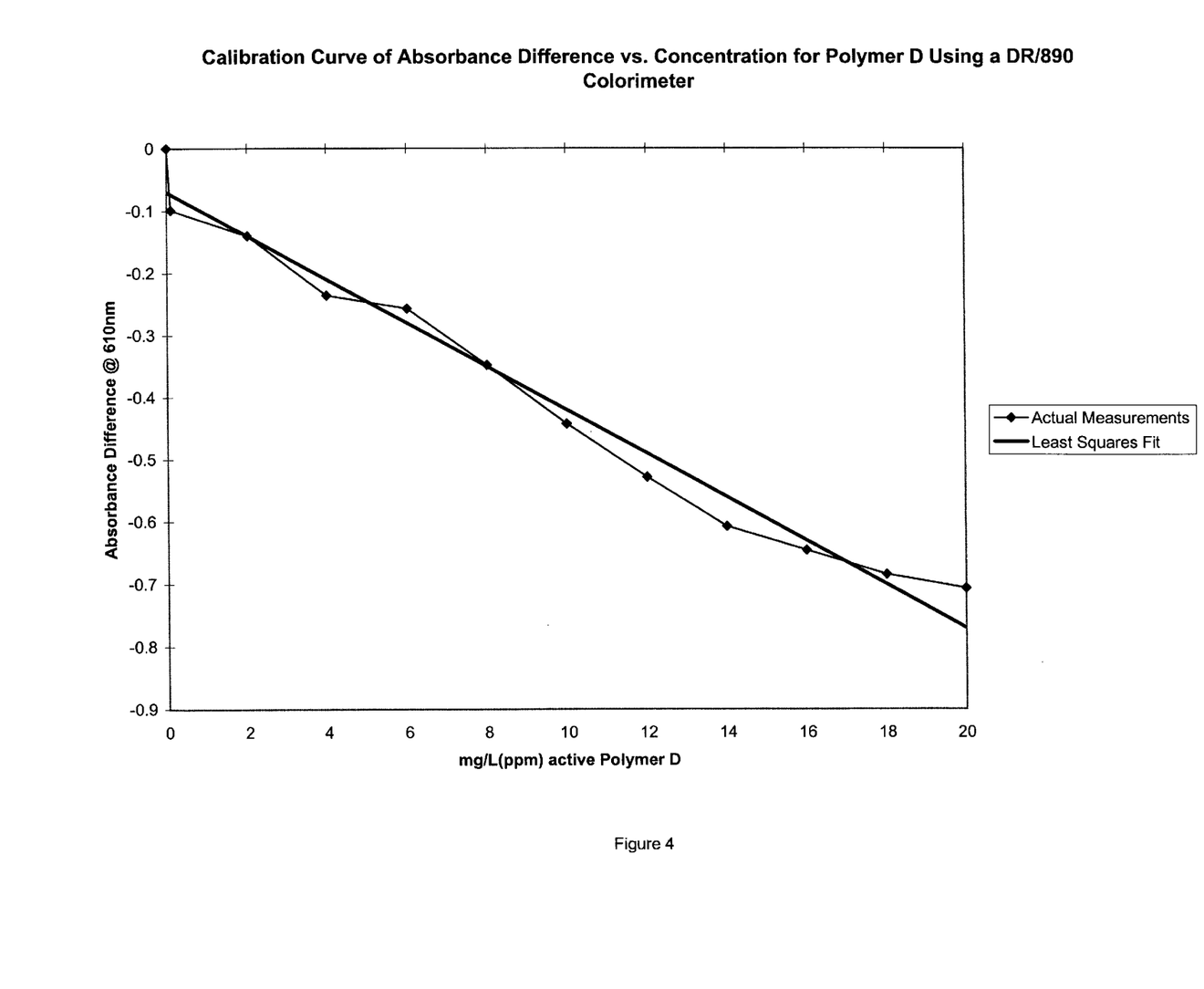
FIG. 4 illustrates, graphically, a calibration curve of absorbance difference versus polymer concentration (in mg/Liter) at 610 nm for Polymer D using a DR/890 Colorimeter. Polymer D is a copolymer of acrylic acid (about 90 mole %) and styrenesulfonic acid, sodium salt(about 10 mole %) with a weight average molecular weight of between about 25,000 and about 50,000 Daltons. One of the lines is a plot of the actual measurements taken, the other line was drawn using a least squares fit to the data.
Figure 5:
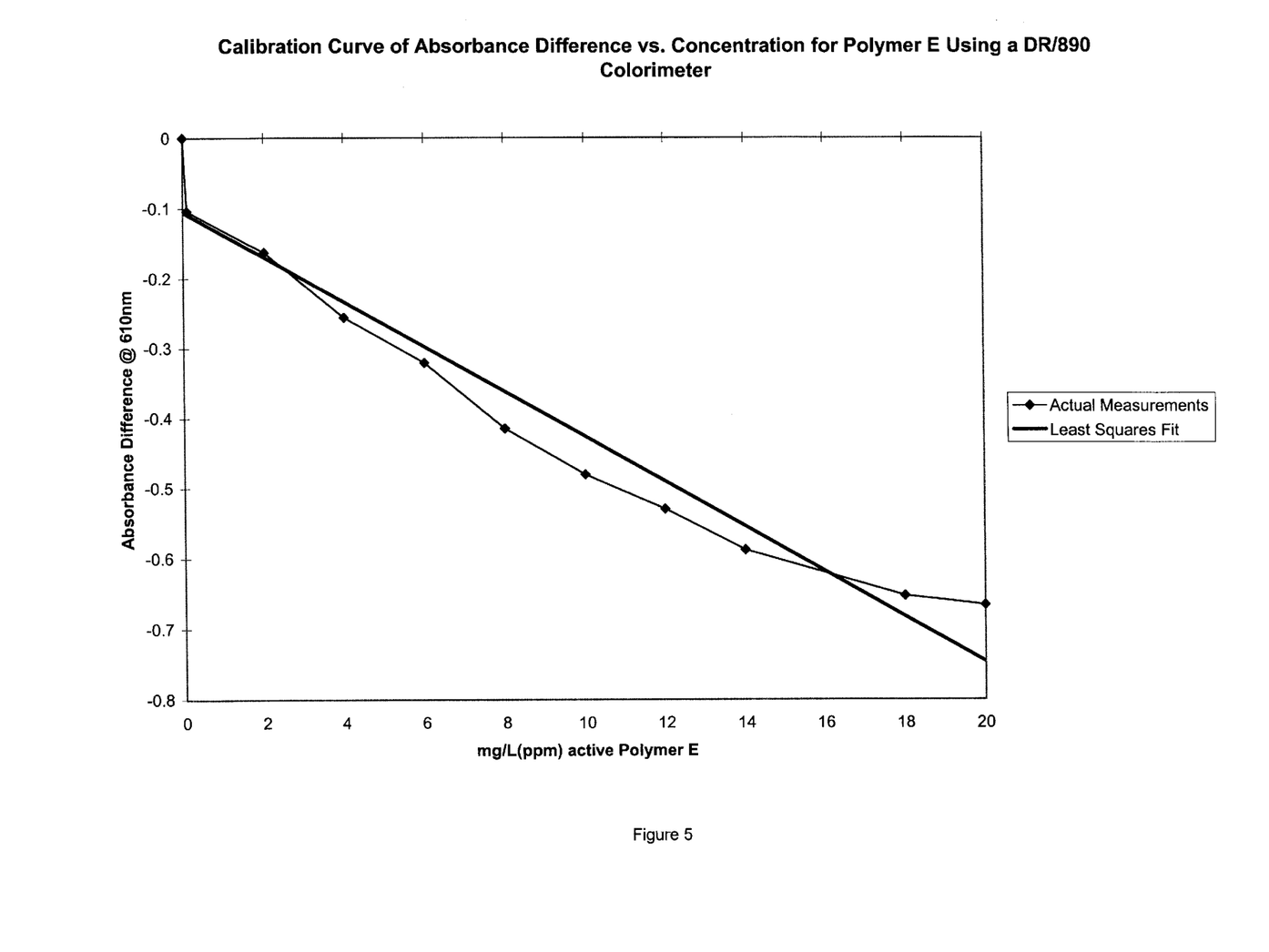
FIG. 5 illustrates, graphically, a calibration curve of absorbance difference versus polymer concentration (in mg/Liter) at 610 nm for Polymer E using a DR/890 Colorimeter. Polymer E is a copolymer of acrylic acid (about 99 mole %) and styrenesulfonic acid, sodium salt (about 1 mole %) with a weight average molecular weight of between about 7000 and about 10,000 Daltons. One of the lines is a plot of the actual measurements taken, the other line was drawn using a least squares fit to the data.
Figure 6:
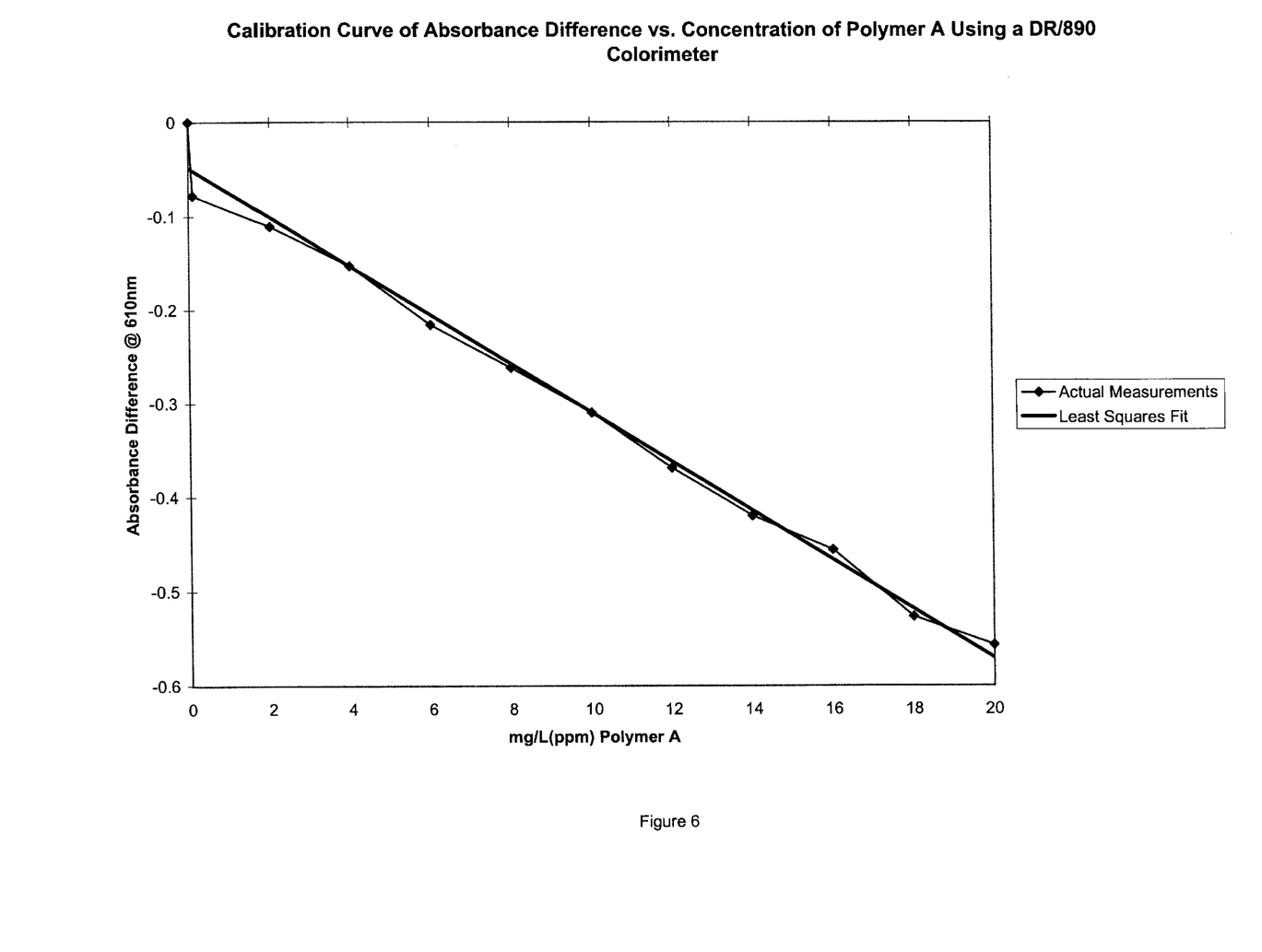
FIG. 6 illustrates, graphically, a calibration curve of absorbance difference versus polymer concentration (in mg/Liter) at 610 nm for Polymer A using a DR/890 Colorimeter. One of the lines is a plot of the actual measurements taken, the other line was drawn using a least squares fit to the data.
Figure 7:
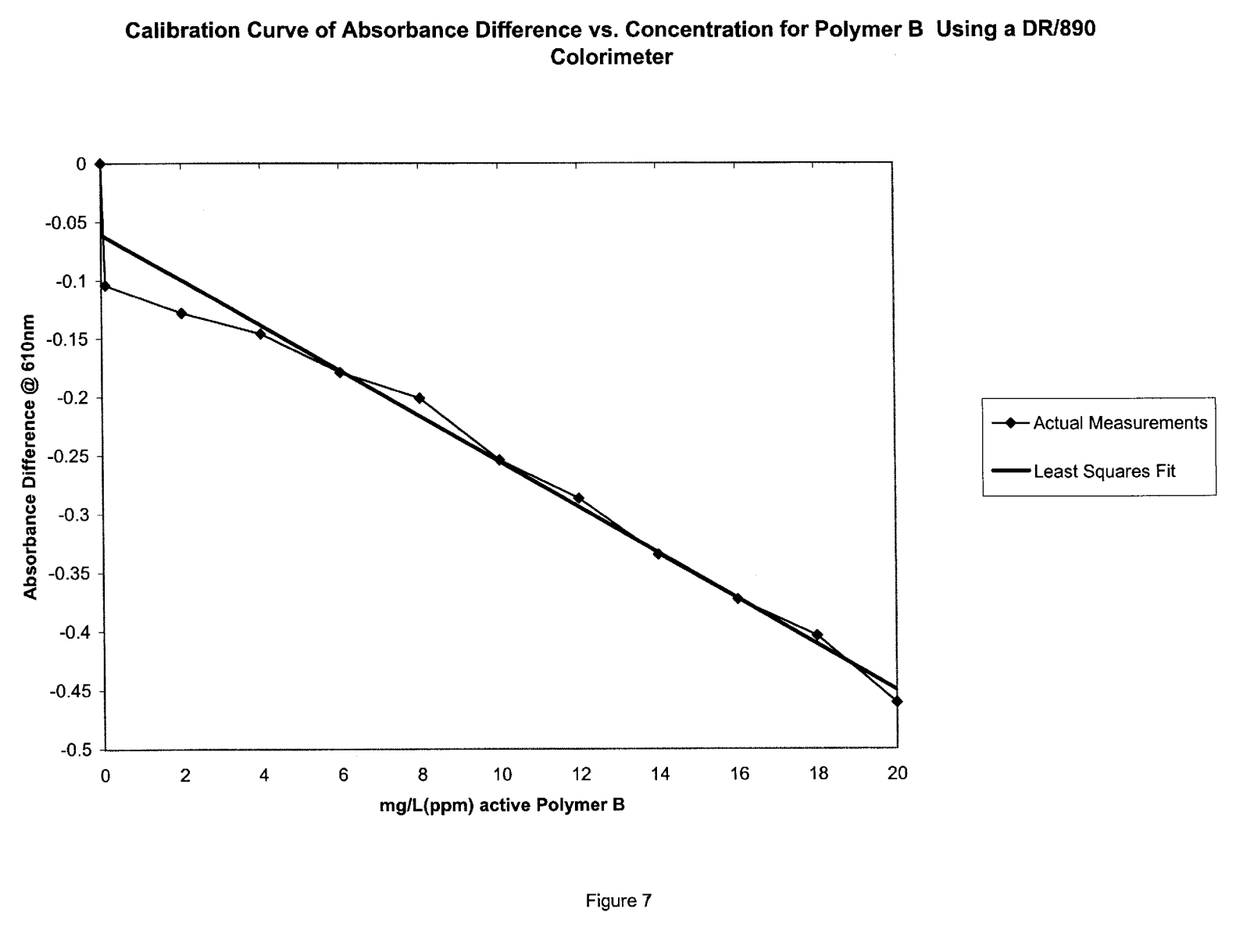
FIG. 7 illustrates, graphically, a calibration curve of absorbance difference versus polymer concentration (in mg/Liter) at 610 nm for Polymer B using a DR/890 Colorimeter. One of the lines is a plot of the actual measurements taken, the other line was drawn using a least squares fit to the data.

The following measurements were taken using the same DR 2010 Spectrophotometer, set at 635 nm with a cell path length of 1 inch on four different pilot cooling tower water samples, containing known amounts of specific anionic polymer. Once the measurement was obtained, it was compared with the calibration curve in FIG. 1 (using the line for actual data) for those samples containing Polymer A and with the calibration curve in FIG. 2 (using the line for actual data) for those samples containing Polymer B:

| Sample | Polymer | Absorbance Difference | ppm active polymer |
|---|---|---|---|
| 1 | A | −0.452 | 12.3 |
| 2 | A | −0.156 | 3.2 |
| 3 | B | −0.467 | 14.9 |
| 4 | B | −0.455 | 14.6 |

Example 2

Making and Testing of A-JARGON

The reagent solution is made the same as in Example 1, except for the fact that no sodium hydroxide is added to the Chelant solution which means the chelant solution made is A-CHELANT. The A-JARGON created has a pH of about 2.8.

A 10 ppm active Polymer A standard and a 10 ppm active Polymer F standard (acrylic acid/acrylamide copolymer, 70:30 mole ratio and weight average molecular weight of about 25,000 to about 40,000) are analyzed using JARGON made as in Example 1 and A-JARGON created according to the description above. The DR/2010 spectrophotometer with a cell path length of 1 inch is set at 635 nm and is used to measure the polymer concentration. Then calibration curves for each polymer tested are consulted to determine the amount of polymer present in each sample. The results are:

| SAMPLE | Amount of Polymer Found using JARGON |
|---|---|
| 10 ppm Polymer A | 10.9 ppm |
| 10 ppm Polymer F | 10.8 ppm |

A similar set of experiments are conducted with Polymers A and F using A-JARGON. The same DR/2010 spectrophotometer is used to measure the polymer concentration based on the amount of sulfonate moiety present in the polymer. Polymer F has 0% mole ratio of sulfonate moiety and Polymer A has ~20% mole ratio of acrylic acid to sulfonate moiety. When A-JARGON is used as the reagent, the sulfonate moiety will be measured; but not the acrylate moiety. The observed and expected concentration of polymer, relative to the results obtained using JARGON are shown in the following table:

| SAMPLE | ACTUAL SULFONATE CONCENTRATION DETERMINED USING A-JARGON | EXPECTED SULFONATE CONCENTRATION |
| --- | --- | --- |
| 10 ppm Polymer A | 1.4 ppm | ~2.0 ppm |
| 20.6 ppm Polymer A | 3.4 ppm | ~4.1 ppm |
| 10 ppm Polymer F | 0.0 ppm | 0.0 ppm |

The A-JARGON results accurately reflects that Polymer F (acrylic acid/acrylamide copolymer) has no sulfonate moiety (or other strongly acidic moiety) present and Polymer A has ~20% mole sulfonate content based on polymer composition considerations.

It should be understood that various changes and modifications to the presently preferred embodiments described herein will be apparent to those skilled in the art. Such changes and i modifications can be made without departing from the spirit and scope of the present invention and without diminishing its attendant advantages. It is therefore intended that such changes and modifications be covered by the appended claims.

What is claimed is:

1. A method for measuring the concentration of an anionically charged polymer in an aqueous solution that comprises the steps of:
    (a) providing a reagent solution comprising
        i) water,
        ii) Nile Blue Dye; and
        iii) chelant, with said chelant being selected from the group consisting of the alkali metal or ammonium salts of phosphonobutane tricarboxylic acid;
    (b) using a suitable device to measure the absorbance of said reagent solution by itself and using this absorbance measurement to zero said suitable device at the level of 0 ppm polymer concentration;
    (c) providing a sample of an aqueous solution containing at least one anionically charged polymer to be tested;
    (d) combining said reagent solution and said sample to create a mixture;
    (e) measuring the absorbance of the mixture using the same suitable device used in step (b); and
    (f) comparing the absorbance of the mixture with the absorbance of samples containing known concentrations of the anionically charged polymers and determining the concentration of anionically charged polymer in the sample therefrom;
wherein the method is conducted without adjusting the pH of said sample and wherein the method further comprises the step of waiting a time period of less than about 7 minutes for said reagent solution and said anionically charged polymer to react between the (d) combining step and the (e) measuring step.

2. A method for measuring the concentration of an anionically charged polymer in an aqueous solution that comprises the steps of:
    (a) providing a reagent solution comprising
        i) water,
        ii) Nile Blue Dye; and
        iii) chelant, which is phosphonobutane tricarboxylic acid;
    (b) using a suitable device to measure the absorbance of said reagent solution by itself and using this absorbance measurement to zero said suitable device at the level of 0 ppm polymer concentration;
    (c) providing a sample of an aqueous solution containing at least one anionically charged polymer to be tested;
    (d) combining said reagent solution and said sample to create a mixture;
    (e) measuring the absorbance of the mixture using the same suitable device used in step (b); and
    (f) determining the concentration of anionically charged polymer containing a measurable amount of at least one strongly acidic moiety;
wherein the method is conducted without adjusting the pH of said sample and wherein the method further comprises the step of waiting a time period of less than about 7 minutes for said reagent solution and said anionically charged polymer to react between the combining step and the measuring step.

3. A reagent solution comprising:
    (i) water, (ii) from about 4.7 ppm to about 9.0 ppm Nile Blue Dye; and
    (iii) from about 55 ppm to about 1100 ppm chelant, with said chelant being selected from the group consisting of the alkali metal or ammonium salts of phosphonobutane tricarboxylic acid.

4. A reagent solution comprising:
    (i) water, (ii) from about 4.7 ppm to about 9.0 ppm Nile Blue Dye; and
    (iii) from about 300 ppm to about 2200 ppm chelant, which is phosphonobutane tricarboxylic acid.

5. The method of claim 1 in which said chelant is 2-phosphonobutane-1,2,4-tricarboxylic acid, sodium salt.

6. The reagent solution of claim 3 in which said chelant is 2-phosphonobutane-1,2,4-tricarboxylic acid, sodium salt.

7. The method of claim 2 in which said chelant is 2-phosphonobutane-1,2,4-tricarboxylic acid.

8. The reagent solution of claim 4 in which said chelant is 2-phosphonobutane-1,2,4-tricarboxylic acid.

9. The method of claim 1 in which said Nile Blue Dye is Nile Blue A.

10. The method of claim 2 in which said Nile Blue Dye is Nile Blue A.

11. The reagent solution of claim 3 in which said Nile Blue Dye is Nile Blue A.

12. The reagent solution of claim 4 in which said Nile Blue Dye is Nile Blue A.

13. The method of claim 5 in which said Nile Blue Dye is Nile Blue A.

14. The reagent solution of claim 6 in which said Nile Blue Dye is Nile Blue A.

15. The method of claim 7 in which said Nile Blue Dye is Nile Blue A.

16. The reagent solution of claim 8 in which said Nile Blue Dye is Nile Blue A.

17. The method of claim 1 in which said time period is less than about 2 minutes.

18. The method of claim 1 in which said time period is less than about 1 minute.

19. The method of claim 1 in which said time period is about 30 seconds.

20. The method of claim 2 in which said time period is about 30 seconds.

* * * * *